United States Patent
Cai et al.

(10) Patent No.: US 11,051,469 B2
(45) Date of Patent: Jul. 6, 2021

(54) POLYPLOID RICE PHOTO-THERMO-SENSITIVE GENETIC MALE STERILE LINE AND BREEDING METHOD THEREOF

(71) Applicants: WUHAN POLYPLOID BIOTECHNOLOGY CO., LTD, Hubei (CN); HUBEI UNIVERSITY, Hubei (CN)

(72) Inventors: Detian Cai, Hubei (CN); Xianhua Zhang, Hubei (CN); Zhaojian Song, Hubei (CN); Wei Wang, Hubei (CN); Yuhua Liu, Hubei (CN); Yuchi He, Hubei (CN)

(73) Assignees: WUHAN POLYPLOID BIOTECHNOLOGY CO., LTD, Hubei (CN); HUBEI UNIVERSITY, Hubei (CN)

( * ) Notice: Subject to any disclaimer, the term of this patent is extended or adjusted under 35 U.S.C. 154(b) by 365 days.

(21) Appl. No.: 15/926,156

(22) Filed: Mar. 20, 2018

(65) Prior Publication Data

US 2018/0206425 A1    Jul. 26, 2018

Related U.S. Application Data

(63) Continuation of application No. PCT/CN2017/095930, filed on Aug. 4, 2017.

(30) Foreign Application Priority Data

Sep. 29, 2016 (CN) .......................... 201610864024.0

(51) Int. Cl.
| | | |
|---|---|---|
| A01H 1/04 | (2006.01) | |
| A01H 1/02 | (2006.01) | |
| A01H 4/00 | (2006.01) | |
| A01H 1/06 | (2006.01) | |
| A01H 6/46 | (2018.01) | |
| A01H 5/10 | (2018.01) | |
| A01H 1/08 | (2006.01) | |

(52) U.S. Cl.
CPC ................ *A01H 1/04* (2013.01); *A01H 1/02* (2013.01); *A01H 1/06* (2013.01); *A01H 1/08* (2013.01); *A01H 4/008* (2013.01); *A01H 5/10* (2013.01); *A01H 6/4636* (2018.05)

(58) Field of Classification Search
CPC ................................ A01H 1/04; A01H 6/4636
See application file for complete search history.

(56) References Cited

FOREIGN PATENT DOCUMENTS

| | | |
|---|---|---|
| CN | 1586134 A | 3/2005 |
| CN | 1817098 A | 8/2006 |
| CN | 1951172 A | 4/2007 |
| CN | 104026006 A | 9/2014 |
| CN | 106386465 A | 2/2017 |
| WO | 2013124844 A1 | 8/2013 |

OTHER PUBLICATIONS

Zhang, X. et al., (2017) Scientific Reports 7:14744; pp. 1-12. (Year: 2017).*
Cai, D. et al. Science in China Series C: Life Sci (Jun. 2007)) vol. 50, No. 3; pp. 356-366. (Year: 2007).*
Zhang, Xianhua, "Studies on the Characteristics of Fertility Alteration in PTGMS Lines WS006 WS012 of Polyploid Rice", (WANFANG Data, May 31, 2011), A Thesis Submitted for the Degree of Master, Hubei University, pp. 1-43, Wuhan China, Presented: May 18, 2009.
Zuo, Bo, "Studies on the Fertility and combination of CMS Lines and Recovery lines of Polyploid Rice", China Excellent Master's Dissertation Database Agricultural Science and Technology, Volume, Jul. 15, 2013, A Thesis Submitted for the Degree of Master, Hubei University, pp. 1-67, Wuhan China, Presented: May 20, 2012.
He, Yuchi et al., "Genome duplication effects on pollen development and the interrelated physiological substances in tetraploid rice with polyploid meiosis stability", Planta, vol. 232, Issue 5, pp. 1219-1228, Published online: Aug. 18, 2010.

* cited by examiner

*Primary Examiner* — Russell Kallis
(74) *Attorney, Agent, or Firm* — Tim Tingkang Xia, Esq.; Locke Lord LLP

(57) ABSTRACT

A breeding method of a polyploid rice photo-thermo-sensitive genetic male sterile line includes determining a diploid rice line with photo-thermo-sensitive genetic male sterility or PMeS characteristic as a parent; carrying out hybridization on a diploid photo-thermo-sensitive genetic male sterile line and a diploid PMeS gene line, carrying out doubling culture on a young ear of a hybrid plant into a hybrid tetraploid; back-crossing the hybrid tetraploid with a tetraploid photo-thermo-sensitive genetic male sterile line; selecting a tetraploid male sterile plants from the back-crossed progeny, self-crossing during a low-temperature and short-day fertile period, and then carrying out composite hybridization with another tetraploid rice line having PMeS gene; selecting tetraploid male sterile plants, and detecting the stability of tetraploid male sterile plants after multiple generations of continuous self-crossing; and determining the stable and consistent tetraploid rice sterile line as the polyploid rice photo-thermo-sensitive genetic male sterile line, named as PSXXX.

4 Claims, 3 Drawing Sheets

POLYPLOID RICE PHOTO-THERMO-SENSITIVE GENETIC MALE STERILE LINE AND BREEDING METHOD THEREOF

CROSS-REFERENCE TO RELATED APPLICATIONS

This application is a continuation application of International Patent Application No. PCT/CN2017/095930, filed Aug. 4, 2017, which itself claims priority to Chinese Patent Application No. 201610864024.0, filed Sep. 29, 2016 in the State Intellectual Property Office of P.R. China, which are hereby incorporated herein in their entireties by reference.

FIELD OF THE INVENTION

The present invention relates generally to the field of new crop variety breeding of modern agriculture, and more particularly to a polyploid rice photo-thermo-sensitive genetic male sterile line and a breeding method thereof.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Heterosis is a common phenomenon in the biological world. The three-line hybrid rice formed from hybridization of three rice lines (male sterile line, male sterile maintainer line and male sterile restorer line) completed by scientists with Yuan Longping as the representative in the 1970s is called as the second green revolution, playing a major role in promoting China's rice production. Since then, Shi Mingsong (1973) found that a Hubei photo-sensitive genetic sterile line has different manifestations of fertility and sterility in male flowers under different day lengths. This sterile line of male sterility under a long-day high-temperature condition and male fertility under a short-day low-temperature condition is called as a photo-thermo-sensitive genetic male sterile line; since this sterile line has two characteristics of sterility and fertility and may have dual purposes in one line, the hybrid formulated by this sterile line and a restorer line is called as a bilinear hybrid.

However, the rice used in the world is all diploid at present. Under the situation of the world's food shortage crisis, there is a need for substantial increase in food production so as to solve the problem of hunger. However, as limited by sexual reproduction and diploidy, rice production has been hovering at a high level for a long time since the 1980s. Thus Cai Detian, Yuan Longping, et al. (2001) proposed a new strategy of "Breeding Super Rice with Dual Advantages of Distant Hybridization and Polyploid", using a three-step strategy to determine heterosis between subspecies, species and genomes of polyploid rice, thus solving the bottleneck problem of low seed setting rate of polyploid rice breeding as the most important issue. Subsequently, the patent technology of combination of tissue culture and colchicine treatment for efficiently inducing formation of polyploid rice and a line with high seed setting rate and "polyploidy meiosis stability (PMeS)" bred are used for breaking the bottleneck problem of low seed setting rate of polyploid rice, thereby bringing the rapid development in polyploid rice breeding. A large number of polyploid rice materials have been formed, and a batch of polyploid rice conventional lines are entering the variety zone trial stage.

If one can make full use of polyploid heterosis to breed polyploid rice sterile lines and polyploid rice restorer lines and to prepare polyploid hybrids, the rice production will be pushed to a new stage, playing an extremely important role in safeguarding the world food security.

Therefore, a heretofore unaddressed need exists in the art to address the aforementioned deficiencies and inadequacies.

SUMMARY OF THE INVENTION

An objective of the present invention is to provide a breeding method of a polyploid rice photo-thermo-sensitive genetic male sterile line.

Another objective of the present invention is to provide a group of polyploid rice photo-thermo-sensitive genetic male sterile lines.

To achieve the above objectives of the present invention, the technical solution adopted in the present invention is as follows:

A breeding method of a polyploid rice photo-thermo-sensitive genetic male sterile line is characterized in that the breeding process comprises the steps:

(a). determining a diploid rice line with photo-thermo-sensitive genetic male sterility or polyploid meiosis stability (PMeS) characteristic as a parent; for example, a typical photo-thermo-sensitive genetic male sterile line Pei' ai 64S (PA64S) is an indica photo-thermo-sensitive genetic male sterile line, Nongken 58S (NK58S) is a japonica photo-thermo-sensitive genetic male sterile line, both having the fertility conversion characteristic of fertility under a short-day low-temperature condition while sterility under a long-day high-temperature condition; however, Huda 9802S (HD9802S) is another indica photo-thermo-sensitive genetic male sterile line, which is affected by light duration with temperature playing a more important role; PA64S, HN58S and HD9802S may be used as a female parent of hybridization; PMeS-1 (Sg99012) and its derived progeny, PMeS-2 (HN2026) and its derived progeny as tetraploid rice lines with PMeS characteristic, as well as corresponding diploid rice lines PMeS-1-2X (Sg99012-2X) and its derived progeny, PMeS-2-2X (HN2026-2X) and its derived progeny also with polyploidy meiosis stability (PMeS) characteristic can be used as a male parent of hybridization;

(b). carrying out hybridization on a diploid photo-thermo-sensitive genetic male sterile line as the female parent and a diploid rice with PMeS characteristic as the male parent to prepare a diploid hybrid rice;

(c). carrying out doubling culture on a young ear of the diploid hybrid rice plant in step b) into a tetraploid hybrid rice; that is, carrying out tissue culture on a young ear of the diploid hybrid rice plant from the second branch differentiation phase to the meiosis phase during young ear differentiation to form a callus with vigorous growth, and then transferring the callus into a doubling culture solution to be cultured and further differentiated into a tetraploid hybrid rice;

(d). back-crossing the tetraploid hybrid rice in step (c) with a tetraploid photo-thermo-sensitive genetic male sterile line, and selecting a tetraploid photo-thermo-sensitive genetic male sterile rice plant from the back-crossed progeny; that is, emasculating the tetraploid hybrid rice during flowering, and back-crossing with the tetraploid photo-thermo-sensitive genetic male sterile line; since the rice photo-thermo-sensitive genetic male sterility is controlled by recessive genes, there are fertile plants in the back-crossed progeny hybrid, thus the rice plants with male sterility and good morphological traits should be selected according to the breeding target;

(e). self-crossing the tetraploid photo-thermo-sensitive genetic male sterile rice plant selected in step (d) during a low-temperature short-day fertile period, then carrying out composite hybridization with another tetraploid rice line having PMeS gene, self-crossing the composite hybridization progeny, and selecting tetraploid photo-thermo-sensitive genetic male sterile rice plants; that is, transferring tetraploid photo-thermo-sensitive genetic male sterile rice plant stumps determined in summer to Hainan or an artificial climate chamber to restore fertility under a low-temperature short-day condition thus self-crossing and seeding, selecting seeding plants under the low-temperature short-day condition from these plants, so as to enable hybrid progeny not only to contain the genetic sterile gene, but also to contain the PMeS gene of high seeding, and selecting the rice plants with male sterility and good morphological traits according to the breeding target;

(f). continuously self-crossing the tetraploid photo-thermo-sensitive genetic male sterile rice plants selected in step (e) by multiple generations (at least 6 to 9 generations) during the low-temperature and short-day fertile period;

(g). detecting the stability of tetraploid photo-thermo-sensitive genetic male sterile rice plants after multiple generations of continuous self-crossing, including the number of chromosomes 4X=48, morphological characteristics of anther sterility, pollen fertility, stigma traits, fertility conversion under a light-temperature condition, and heterogamety and heterosis after hybridization with tetraploid restorer lines, wherein tetraploid rice generally has the morphological characteristics of stout stalks and dark green leaves, a root tip chromosome is observed to determine 4X=48 as tetraploid (FIG. 1); the anther of a tetraploid male sterile line is not much larger than the anther of a diploid sterile line, but still is milky and arrow-shaped (FIG. 2), microscopically observed after staining with 0.05% $I_2$-KI, the tetraploid sterile plants have round large black pollen in the fertile period, but have deformed pollen in pale yellow or very light gray black in the sterile period (FIG. 3), the sterile plants with more developed pistil stigma in flowers, about 40% unilateral exposure rate and obvious fertility conversion characteristic under different temperature-light conditions are selected, and once entering the sterile period, the sterility is stable without returning to fertility for 25 days or more whereas having a seed setting rate of 40% or more under the short-day low-temperature condition during the fertile period, in addition, it is easy to obtain hybrid seeds after test cross of the sterile plants and tetraploid restorer lines having restorability, the planted hybrid thereof having stronger heterosis than its male parent and female parent;

(h). determining the stable and consistent tetraploid photo-thermo-sensitive genetic male sterile rice as the polyploid rice photo-thermo-sensitive genetic male sterile line, wherein after multiple detection and comparison in step (g), the selected male sterile line with stable and consistent morphological characteristics, stable sterility (sterility rate of 100%, and sterility degree of 99.5%), high setting rate during the fertile period (>40%), good heterogamety, and strong heterosis is determined as the tetraploid rice photo-thermo-sensitive genetic male sterile line, and named as PSXXX-4x, where XXX is a figure.

In the above solution, the diploid photo-thermo-sensitive genetic male sterile line is selected from the following lines: Pei' ai 64S (PA64S), Nongken 58S (Nongken 58S) and HD9802S.

In the above solution, the diploid rice with PMeS characteristic is selected from the following lines: PMeS-1-2X (Sg99012-2X), PMeS-2-2X (HN2026-2X), derived progeny of PMeS-1-2X (Sg99012-2X), and PMeS-2-2X (HN2026-2X).

In the above solution, the tetraploid photo-thermo-sensitive genetic male sterile line for back-crossing in step d) is obtained through the following method: carrying out doubling culture on a young ear of the diploid photo-thermo-sensitive genetic male sterile line plant as the male parent into a tetraploid photo-thermo-sensitive genetic male sterile line.

In the above solution, the tetraploid rice for composite hybridization in step e) is selected from the following tetraploid rice lines with the PMeS gene: HN128-4X, HN164-4X, A175-4X.

The tetraploid rice photo-thermo-sensitive genetic male sterile line obtained by using the breeding method of a polyploid rice photo-thermo-sensitive genetic male sterile line has the characteristics of stable and consistent morphological characteristics, stable sterility (sterility rate of 100%, and sterility degree of 99.5%), high setting rate during a fertile period (>40%), good heterogamety, and strong heterosis, and is named as PSXXX, where XXX is a figure.

The rice varieties/rice lines involved in the breeding method of the present invention are derived from the existing disclosed rice varieties/rice lines and derived lines thereof:

Pei' ai 64S (PA64S): Pei' ai 64S is an indica rice low temperature-sensitive male sterile line bred by taking Nongken 58S as the female parent and Pei' ai 64 as the male parent for hybridization, selecting genetic sterile plants similar to Pei' ai 64 in $F_2$ and then back-crossing with Pei' ai 64, carrying out dual selection on the hybrid progeny thereof by multiple generations in Changsha and Hainan.

Nongken 58S (NK58S): Nongken 58S is a japonica photo-sensitive genetic sterile line bred from a japonica variety "Nongken 58" by Chinese scientist Shi Mingsong in 1973.

Huda 9802S (HD9802S): Huda 9802S is an early indica thermo-sensitive genetic sterile line bred by College of Life Sciences of Hubei University taking "Huda 51" as the female parent and "Hongfuzao" as the male parent for hybridization through breading and low-temperature screening by multiple generations.

PMeS-1 (Sg99012): PMeS-1 (Sg99012) is a polyploid rice line PMeS-1 with tetraploid meiosis stability (PMeS) bred from the polyploid progenies of indica and japonica hybrids by College of Life Sciences of Hubei University through several years of indica-japonica hybridization and back-crossing selection and detection, published in the journal "Cai Detian, Chen Jianguo, Chen Dongling, et al. Breeding of two polyploid rice lines with polyploidy meiosis stability. Science China, 2007,37 (2): 217-226".

PMeS-2 (HN2026): PMeS-2 (HN2026) is a tetraploid rice line PMeS-2 with polyploid meiosis stability (PMeS) bred from the polyploid progenies of indica and japonica hybrids by College of Life Sciences of Hubei University, published in the journal "Cai Detian, Chen Jianguo, Chen Dongling, et al. Breeding of two polyploid rice lines with polyploidy meiosis stability. Science China, 2007,37 (2): 217-226".

HN164-4X: HN164-4X is the derived progeny polyploid rice line HN164-4X with meiosis stability and excellent agronomic traits bred by College of Life Sciences of Hubei University taking the polyploid rice line PMeS-1 (Sg99012) with polyploidy meiosis stability as the parent.

HN128-4X: HN128-4X is the derived progeny polyploid rice line HN164-4X with meiosis stability and excellent agronomic traits bred by College of Life Sciences of Hubei University taking the polyploid rice line PMeS-1 (Sg99012) with polyploidy meiosis stability as the parent.

A175-4X: A175-4X is the derived progeny polyploid rice line A175-4X with meiosis stability and excellent agronomic traits bred by College of Life Sciences of Hubei University taking the polyploid rice line PMeS-2 (HN2026) with polyploidy meiosis stability as the parent.

The present invention has the following beneficial effects that the present invention solves the bottleneck problem of low setting rate of polyploid rice by changing a diploid photo-thermo-sensitive genetic male sterile line from diploid to tetraploid, and carrying out hybridization with a line having polyploid meiosis stability (PMeS), thereby obtaining a tetraploid rice photo-thermo-sensitive genetic male sterile line of high setting rate during photo-thermo-sensitive sterile and fertile periods, which can be used for the breeding of tetraploid rice hybrids.

More than 625 seeds for each of (1) the diploid photo-thermo-sensitive genetic male sterile line, HD9802S, (2) the diploid rice with PMeS characteristic, HN2026-2X, (3) the tetraploid rice line with the PMeS gene, HN164-4X, and (4) the rice photo thermo sensitive genetic male sterile line PS006, were stored/deposited under CCTCC Nos: P202106, P202105, P202101, and P202107, respectively, on Dec. 10, 2020, under the terms of the Budapest Treaty in the China Center for Type Culture Collection at Wuhan University, Wuhan 430072, P. R. China, one of recognized International Depository Authorities (IDAs). The seeds will be irrevocably and without restriction or condition released to the public upon the issuance of a patent would satisfy the deposit requirement made herein.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
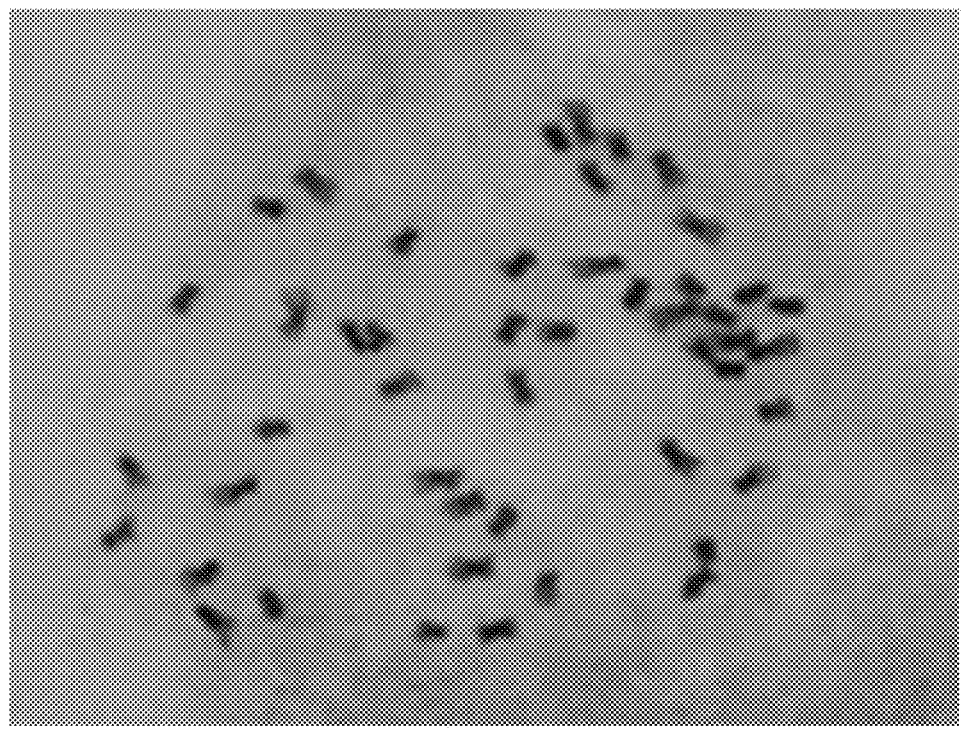
FIG. 1 is root tip chromosomes of a tetraploid photo-thermo-sensitive genetic male sterile line (2n=4x=48).

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more". The word "exemplary" is used herein to mean "serving as an example, instance, or illustration". Any aspect described herein as "exemplary" is not necessarily to be construed as preferred or advantageous over other aspects. Unless specifically stated otherwise, the term "some" refers to one or more. Combinations such as "at least one of A, B, or C", "one or more of A, B, or C", "at least one of A, B, and C", "one or more of A, B, and C", and "A, B, C, or any combination thereof" include any combination of A, B, and/or C, and may include multiples of A, multiples of B, or multiples of C. Specifically, combinations such as "at least one of A, B, or C", "one or more of A, B, or C", "at least one of A, B, and C", "one or more of A, B, and C", and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module", "mechanism", "element", "device" and the like may not be a substitute for the word "means". As such, no claim element is to be construed as a means plus function unless the element is expressly recited using the phrase "means for". It should also be understood that one or more steps within a method may be executed in different order (or concurrently) without altering the principles of the invention.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

Typically, terms such as "about," "approximately," "generally," "substantially," and the like unless otherwise indicated mean within 20 percent, preferably within 10 percent, preferably within 5 percent, and even more preferably within 3 percent of a given value or range. Numerical quantities given herein are approximate, meaning that the term "about," "approximately," "generally," or "substantially" can be inferred if not expressly stated.

The description is now made as to the embodiments of the invention in conjunction with the accompanying drawings. It should be understood that specific embodiments described herein are merely intended to explain the invention, but not intended to limit the invention. Various modifications to these aspects will be readily apparent to those skilled in the art, and the generic principles defined herein may be applied to other aspects.

Embodiment 1: Breeding process of tetraploid rice photo-thermo-sensitive genetic male sterile line PS006

Figure 5:
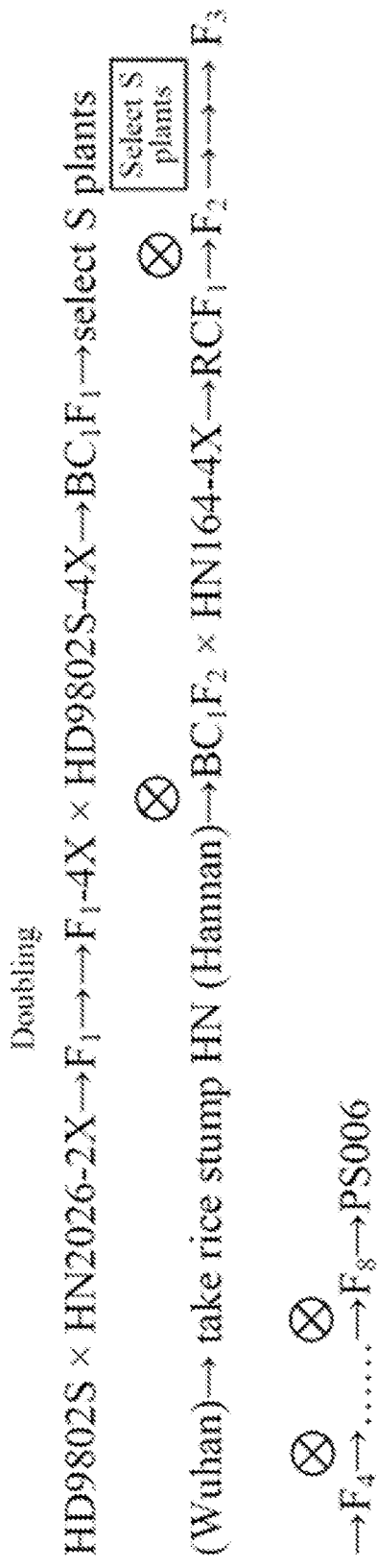
FIG. 5 shows a tetraploid rice photo-thermo-sensitive genetic male sterile line PS006, where S is the abbreviation for photo-thermo-sensitive genetic male sterile line.

Breeding process chart of tetraploid rice sterile line PS006 is shown in FIG. 5.

Doubling
HD9802S x HN2026-2X→→$F_1$-4X×HD9802S-4X→$BC_1F_1$→select S plants

Figure 2:
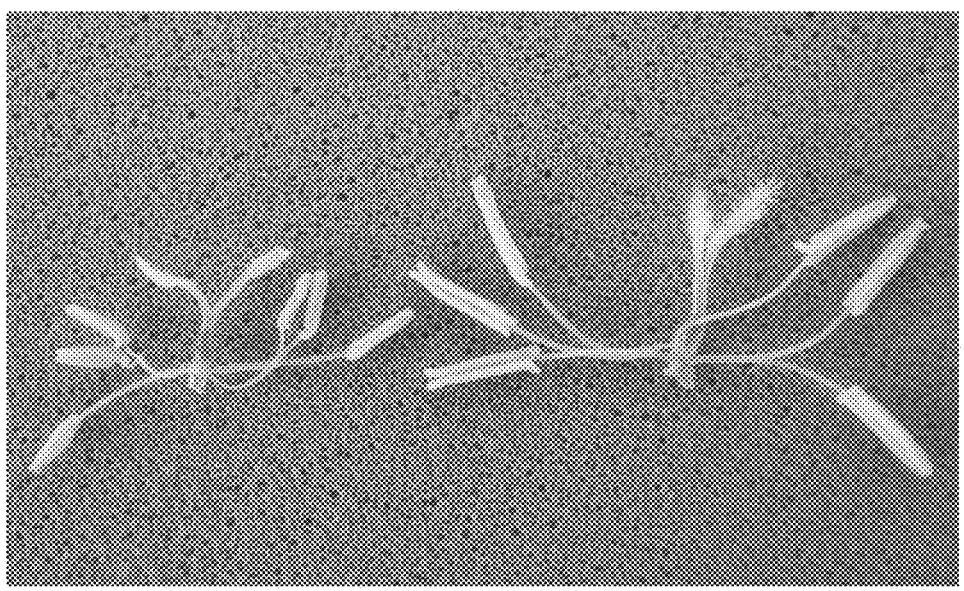
FIG. 2 is a comparison of floral organs of a diploid photo-thermo-sensitive genetic male sterile line and a tetraploid photo-thermo-sensitive genetic male sterile line, wherein the left is a diploid floral organ and the right is a tetraploid floral organ.
Figure 3:
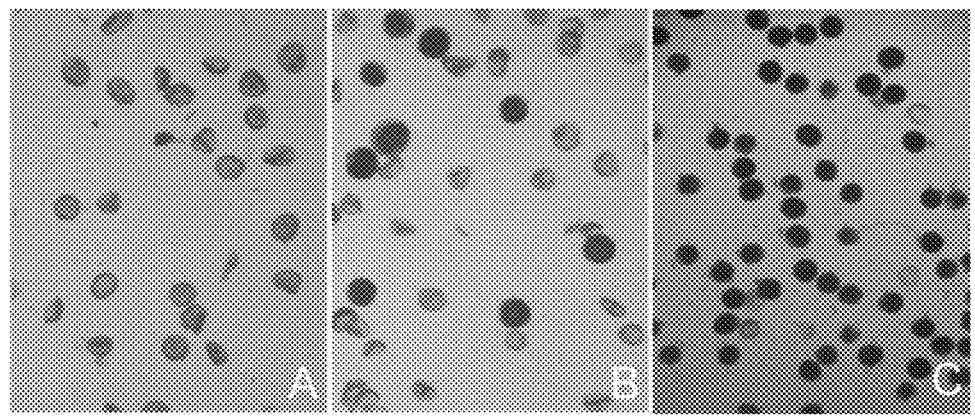
FIG. 3 is the pollen fertility of a tetraploid rice photo-thermo-sensitive genetic male sterile line, wherein A is sterile period; B is fertility conversion period; and C is fertile period.
Figure 4:
FIG. 4 is tetraploid rice photo-thermo-sensitive genetic male sterile line plants.

Description of breeding process: (a). determining HD9802S with photo-thermo-sensitive genetic male sterility and rice line HN2026 with polyploid meiosis stability (PMeS) as parents; (b). carrying out hybridization on a diploid photo-thermo-sensitive male sterile line with a diploid PMeS line, that is, using the diploid sterile line HD9802S and HN2026-2X to carry out hybridization; (c). carrying out doubling culture on a young ear of $F_1$ hybrid plant into a hybrid tetraploid, that is, carrying out tissue culture on a young ear of a hybrid plant of HD9802S×HN2026-2X from the second branch differentiation phase to the meiosis phase during young ear differentiation to form a callus with vigorous growth, and then transferring the callus into a doubling culture solution to be cultured and further differentiated into tetraploid hybrid $F_1$-4X; (d). back-crossing $F_1$-4X with tetraploid photo-thermo-sensitive genetic male sterile line HD9802S-4X, that is, emasculating the doubled hybrid plants during flowering, and back-crossing with the photo-thermo-sensitive genetic male sterile line tetraploid HD9802S-4X (HD9802S-4X is doubled from young ears of HD9802S plants) to obtain back-crossing hybrid generation 1 $BC_1F_1$; (e). selecting tetraploid genetic male sterile plants (S plants, Wuhan) from back-crossed progeny; (f). in order to determine the fertility of selected tetraploid genetic male sterile plants during a low-temperature short-day fertile period, transferring the sterile plant rice stumps determined in summer to Hainan to restore fertility under the low-temperature short-day condition thus self-crossing and seeding to obtain $BC_1F_2$; (g). carrying out composite hybridization on $BC_1F_2$ with another tetraploid rice line HN164-4X (derived progeny of Sg99012) having PMeS gene to obtain $RCF_1$, and self-crossing $RCF_1$ to obtain $RCF_2$ (abbreviated as $F_2$); (h). selecting S plants therefrom for self-crossing into $F_3$, then self-crossing male sterile plant lines to obtain $F_4$, thus self-crossing continuously by 6 generations to obtain $F_8$, that is, selecting sterile plants in Wuhan, and taking rice stumps to Hainan for continuous self-crossing by 6 generations to obtain $F_8$; (i). detecting the stability of generation $F_8$ tetraploid photo-thermo-sensitive genetic male sterile line, including the number of chromosomes (4X=48), morphological characteristics of anther sterility, pollen fertility, stigma traits, fertility conversion under a light-temperature condition, and heterogamety and heterosis after hybridization with tetraploid restorer lines, wherein a root tip chromosome is observed to determine 4X=48 as tetraploid (FIG. 1), the anther of a tetraploid male sterile line is not much larger than the anther of a diploid sterile line, but still is milky and arrow-shaped (FIG. 2), microscopically observed after staining with 0.05% $I_2$-IK, the tetraploid sterile plants have round large black pollen in the fertile period, but have deformed pollen in pale yellow or very light gray black in the sterile period (FIG. 3), the sterile plants with more developed pistil stigma in flowers, about 40% unilateral exposure rate and obvious fertility conversion characteristic under different temperature-light conditions are selected, and the sterility is stable without returning to fertility for 25 days or more, whereas having a seed setting rate of 40% or more under the short-day low-temperature condition during the fertile period, in addition, it is easy to obtain hybrid seeds after test cross of the sterile plants and tetraploid restorer lines having restorability (the outcrossing rate is 35% to 45%), the planted hybrid thereof having stronger heterosis than its male parent and female parent; (j). determining the stable and consistent tetraploid rice sterile line as the polyploid rice photo-thermo-sensitive genetic male sterile line, wherein after multiple detection and comparison in step (i), the selected male sterile line with stable and consistent morphological characteristics, stable sterility (sterility rate of 100%, and sterility degree of 99.5%), high setting rate during the fertile period (>40%), good heterogamety, and strong heterosis is determined as the tetraploid rice photo-thermo-sensitive genetic male sterile line, and named as PS006, the tetraploid rice PS006 having the morphological characteristics of stout stalks and dark green leaves, while being neat and consistent (FIG. 4).

Embodiment 2: Description of breeding process of tetraploid rice sterile line PS012

Figure 6:
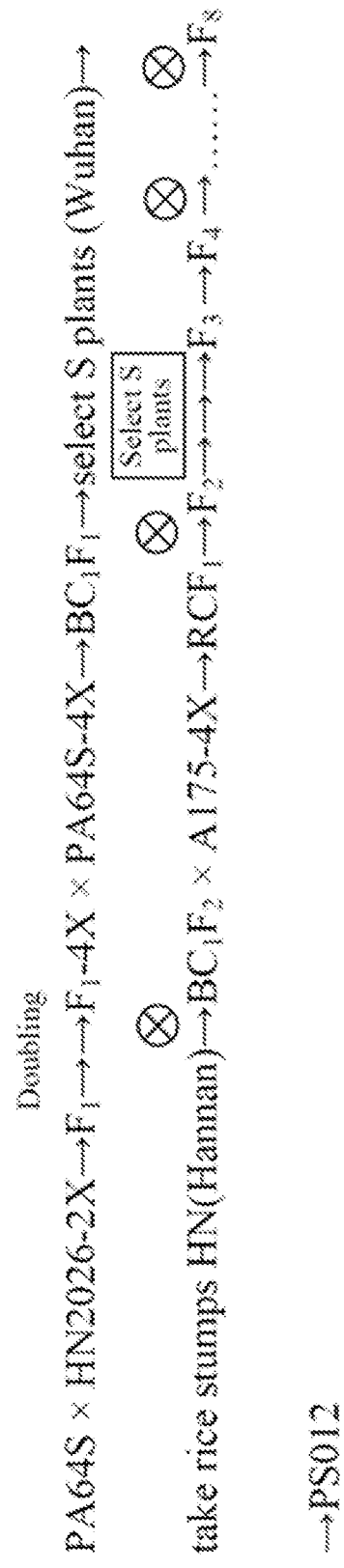
FIG. 6 shows a tetraploid rice sterile line PS012, where S is the abbreviation for photo-thermo-sensitive genetic male sterile line.

Breeding process chart of tetraploid rice sterile line PS012 is shown in FIG. 6.

Doubling
PA64S×HN2026–2X→$F_1$→→$F_1$–4X→$BC_1F_1$→select S plants (Wuhan)→

Description of breeding process: (a). determining PA64S with photo-thermo-sensitive genetic male sterility and rice line HN2026-2X with polyploid meiosis stability (PMeS) as parents; (b).carrying out hybridization on a diploid photo-thermo-sensitive male sterile line with a diploid PMeS line, that is, using the diploid sterile line PA64S and HN2026-2X to carry out hybridization; (c). carrying out doubling culture on a young ear of $F_1$ hybrid plant into a hybrid tetraploid $F_1$-4X, that is, carrying out tissue culture on a young ear of a hybrid plant of PA64S×HN2026-2X from the second branch differentiation phase to the meiosis phase during young ear differentiation to form a callus with vigorous growth, then transferring the callus into a doubling culture solution to be cultured and further differentiated into tetraploid hybrid $F_1$-4X; (d). back-crossing tetraploid hybrid $F_1$-4X with photo-thermo-sensitive genetic male sterile line tetraploid, that is, emasculating the doubled hybrid plants during flowering, and back-crossing with the photo-thermo-sensitive genetic male sterile line tetraploid PA64S-4X (PA64S-4X is doubled from young ears of PA64S plants) to obtain back-crossing hybrid generation 1 $BC_1F_1$; (e). selecting tetraploid genetic male sterile plants (S plants, Wuhan) from back-crossed progeny; (f). in order to determine the fertility of selected tetraploid genetic male sterile plants during a low-temperature short-day a fertile period, transferring the sterile plant rice stumps determined in summer to Hainan to restore fertility under the low-temperature short-day condition thus self-crossing and seeding to obtain $BC_1F_2$; (g). carrying out composite hybridization on $BC_1F_2$ with another tetraploid rice line A175-4X (derived progeny of HN2026) having PMeS gene to obtain $RCF_1$, and self-crossing $RCF_1$ to obtain $RCF_2$ (abbreviated as F2); (h). selecting S plants therefrom for self-crossing into $F_3$, then self-crossing male sterile plant lines to obtain $F_4$, thus self-crossing continuously by 6 generations to obtain $F_8$, that is, selecting sterile plants in Wuhan, and taking rice stumps to Hainan for continuous self-crossing by 6 generations to obtain $F_8$; (i). detecting the stability of generation $F_8$ tetraploid photo-thermo-sensitive genetic male sterile line, including the number of chromosomes (4X=48), morphological characteristics of anther sterility, pollen fertility, stigma traits, fertility conversion under a light-temperature condition, and heterogamety and heterosis after hybridization with tetraploid restorer lines; (j). determining the stable and consistent tetraploid rice sterile line as the polyploid rice photo-thermo-sensitive genetic male sterile line, after multiple detection and comparison in step (i), the selected male sterile line with stable and consistent morphological characteristics, stable sterility (sterility rate of 100%, and sterility degree of 99.5%), high setting rate during the fertile period (>40%), good heterogamety, and strong heterosis is determined as tetraploid rice photo-thermo-sensitive genetic male sterile line, and abbreviated as PS012.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A breeding method of a polyploid rice photo-thermo-sensitive genetic male sterile line, characterized in that the breeding process comprises the steps:
    (a) determining a diploid rice line with photo-thermo-sensitive genetic male sterility or polyploid meiosis stability (PMeS) characteristic as a parent;
    (b) carrying out hybridization on a diploid photo-thermo-sensitive genetic male sterile line as the female parent and a diploid rice with the PMeS characteristic as the male parent to prepare a diploid hybrid rice, wherein the diploid photo-thermo-sensitive genetic male sterile line is HD9802S, and sample of seed of said HD9802S is deposited under CCTCC No: P202106; and the diploid rice with the PMeS characteristic is HN2026-2X, and sample of seed of said HN2026-2X is deposited under CCTCC No: P202105;

(c) carrying out doubling culture on a young ear of the diploid hybrid rice in step (b) into a tetraploid hybrid rice;

(d) back-crossing the tetraploid hybrid rice in step (c) with a tetraploid photo-thermo-sensitive genetic male sterile line, and selecting a tetraploid photo-thermo-sensitive genetic male sterile rice from the back-crossed progeny;

(e) self-crossing the tetraploid photo-thermo-sensitive genetic male sterile rice selected in step (d) during a low-temperature short-day fertile period, then carrying out composite hybridization on the self-crossed progeny with another tetraploid rice line having PMeS gene, self-crossing the composite hybridization progeny, and selecting a tetraploid photo-thermo-sensitive genetic male sterile rice, wherein said another tetraploid rice for the composite hybridization is a tetraploid rice line with the PMeS gene of HN164-4X, and sample of seed of said HN164-4X is deposited under CCTCC No: P202101;

(f) continuously self-crossing the tetraploid photo-thermo-sensitive genetic male sterile rice selected in step (e) by multiple generations during the low-temperature and short-day fertile period;

(g) detecting the stability of tetraploid photo-thermo-sensitive genetic male sterile rice in step (f) after multiple generations of continuous self-crossing, including the number of chromosomes 4X=48, morphological characteristics of anther sterility, pollen fertility, stigma traits, fertility conversion under a light-temperature condition, and heterogamety and heterosis after hybridization with tetraploid restorer lines; and (h) determining stable and consistent tetraploid photo-thermo-sensitive genetic male sterile rice as the polyploid rice photo-thermo-sensitive genetic male sterile line, wherein the polyploid rice photo-thermo-sensitive genetic male sterile line is named as PS006, and a representative sample of seed of said PS006 is deposited under CCTCC No: P202107.

2. The breeding method of a polyploid rice photo-thermo-sensitive genetic male sterile line according to claim 1, characterized in that the tetraploid photo-thermo-sensitive genetic male sterile line for back-crossing in step (d) is obtained through carrying out doubling culture on a young ear of the diploid photo-thermo-sensitive genetic male sterile line plant as the female parent into a tetraploid photo-thermo-sensitive genetic male sterile line.

3. The breeding method of a polyploid rice photo-thermo-sensitive genetic male sterile line according to claim 1, characterized in that the continuous self-crossing by multiple generations is continuous self-crossing by at least 6 to 9 generations.

4. A tetraploid rice photo-thermo-sensitive genetic male sterile line bred by using the breeding method of a polyploid rice photo-thermo-sensitive genetic male sterile line according to claim 1, being named as PS006, wherein the representative sample of seed of said PS006 is deposited under CCTCC No: P202107.

* * * * *